US00PP23573P3

(12) United States Plant Patent
Dorsey

(10) Patent No.: US PP23,573 P3
(45) Date of Patent: Apr. 30, 2013

(54) LATE HARVEST AVOCADO TREE

(50) Latin Name: *Persea americana*
Varietal Denomination: Buck 3

(76) Inventor: Charlie Dorsey, Homestead, FL (US)

( * ) Notice: Subject to any disclaimer, the term of this patent is extended or adjusted under 35 U.S.C. 154(b) by 51 days.

(21) Appl. No.: 12/925,213

(22) Filed: Oct. 18, 2010

(65) Prior Publication Data

US 2012/0096611 P1 Apr. 19, 2012

(51) Int. Cl.
*A01H 5/00* (2006.01)

(52) U.S. Cl. ..... Plt./200

(58) Field of Classification Search ..... Plt./200
See application file for complete search history.

*Primary Examiner* — Kent L Bell
(74) *Attorney, Agent, or Firm* — Mark C. Jacobs

(57) ABSTRACT

A new avocado tree has an intermediate growth pattern, with fruit that mature from the end of March through mid-May. The fruit are found in a diversity of shapes, and large lenticels are found on the skin as the fruit ripens.

6 Drawing Sheets

Field of the plant: This plant patent pertains to the *Persea americana*, or Avocado.

BACKGROUND OF THE VARIETY

The present invention relates to a new and distinct variety of avocado tree which is characterized by its ability to have two fruit pickings, of good eating quality and relatively late picking and more particularly characterized by the fruit being easily stored on the tree.

The avocado season in Florida, and especially south Florida in Dade and Broward counties, runs from late May of this year, 2010, till March of next year 2011. A relatively small amount of avocados are available for the marketplace from Mid-March of the year following through late May of next year.

The popularity of Mexican food is ever increasing and as such the market for Florida avocados has been expanding at a rapid pace, throughout the calendar year. The variety of this invention has been named 'Buck 3', as a tribute to the Inventor's son, whose nickname was Buck, has a late maturation of the fruit, later than either the 'Alfa' or 'Wheeling' varieties.

ORIGIN AND ASEXUAL REPRODUCTION OF THE VARIETY

The original tree was found as a bud sport mutation of one limb of a 'Choquette' avocado tree on Applicant's property in Dade County, south of Miami, Fla. It was asexually reproduced in March 2005 by the grafting of bud stock from the parent tree onto 'Walden' root stock and named for applicant's son.

SUMMARY OF THE NEW VARIETY

The original tree and the asexually reproduced progeny are moderately large in both width-spread-and height. It is characterized further by its Type "B" flowers and excellent fruit set. The growth pattern of the tree is intermediate. The fruit mature from the end of March through mid-May when very few avocados are available in the marketplace in South Florida. The fruit is seen to have a diversity of shapes.

DETAILED DESCRIPTION OF THE VARIETY

Figure 1:
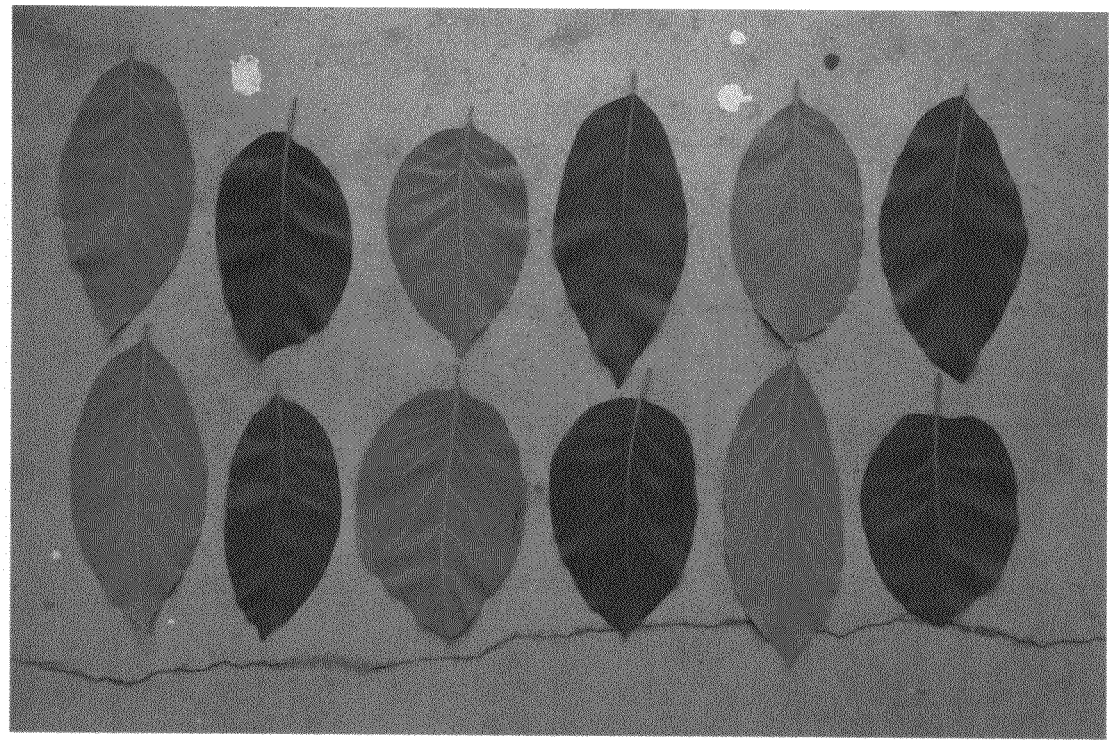
FIG. 1 is a color photograph showing the dark green upper surface of the leaves of this avocado tree and the light green under surface of various shaped leaves of the avocado tree of this application.

Reference is now made to the botanical details of the new and distinct variety of avocado tree. Major color code plate identification are made by reference to the A. Maerz and M. Paul Dictionary of color published by McGraw Hill Company, Second Edition, 1950, as well as common accepted color terminology.

Tree: The seedling tree is moderately large, broad and tall, that is 7 feet to 8 feet wide and 10 feet tall. Several years later it had grown to about 15 feet wide by 20 feet tall. The growth pattern is intermediate or spreading. It was first described in 2007 and again in 2009 in South Florida. Trunk diameters range from about 8 inches to 12 inches and the observed one was 9.8 inches at an elevation of 3 feet. The main trunk bark is dark brown, 7.5YR (5/4) and its secondary branches are colored 5Y (7/4).

Leaves:

*Size and shape*.—Fairly large, resembling Guatemalan type or hybrid leaves. Leaves are ovate to ovoid in shape. The leaves are broad with a rounded base and intermediate to obtuse-pointed tips. The leaves are sparsely pubescent. The leaves are arranged at an angle of 45-47 degrees. The leaf base is acute to obtuse, leaf tip acute; pubescence & sparse. Leaf blades are of an average length of 22.2 cm (8 12/16 inch) and width of 11.8 cm (4 10/16 inch). The length/width ratio averages 1.9. The leaves are arranged alternatively along the stems. As to color, the upper surface of the leaf color ranges from stock green to forest green or 003333 to 003300 (Coutsoukis, 2004) whereas the lower surface color ranges from odd green to seas spray (Hall Color Charts, 2004) or 336600 to 336633 (Coutsoukis , 2004). The leaf petiole and main veins are canary yellow (Hall Color Charts, 2004) or 669900 (Coutsoukis, 2004).

*Venation*.—The leaf margins are entire with 13 to 16 primary veins. Leaf texture is semi-hard. The venation relief on the upper leaf surface is slightly raised and that of the lower surface intermediately raised.

*Petioles*—3.3 to 4.3 cm (1.3 to 1.7 inch) long. The upper surface leaf color ranges from stock green to forest green or 003333 to 003300 (Coutsoukis, 2004) whereas the lower surface color ranges from odd green to seas spray (Hall Color Charts, 2004) or 336600 to 336633 (Coutsoukis, 2004). The leaf petiole and main veins are canary yellow (Hall Color Charts, 2004) or 669900 (Coutsoukis, 2004). The mean diameter of the base of the leaf petiole is 4.8 mm (3/16 inch) with a range of 4.3 mm to 5.3 mm (2/16 to 3/16 inch). There is little to no anise odor when the leaves are crushed as is the case with other varieties.

Flowers: Type B, stamens which open in the morning. The bloom season is late February to early April. The estimated number of flowers per tree is about 300,000. Inflorescences are panicles (multiple flowers) which end in a vegetative bud. The flowers are in an alternate position within each sub-panicle, with 2 to 3 flowers per site. Some flowers exhibit an overlap at about noon between the two stages. Flowers are often held on lateral inflorescences (thyrse) carried in a pseudo-terminal position on the indeterminate shoots. Some sub-branches of the inflorescence are terminated by 3 flowers, the center one being typically larger than the 2 lateral ones.

*Flower buds*.—Ovoid shape to a little elongated preanthesis. Size is age dependent, with expected variation for typical young, middle size and near opening, range from 0.091 to 0.21 in length and from 0.073 to 0.169 inches in diameter. Observed ones were within these ranges. Color varies with age, with young buds being 2.5GY (6/6) medium size, are 2.5GY (7/6) and before opening they are 2.5GY (7/8).

*Petals & sepals*.—Petals and sepals are both 3 in number and of same color and shape, and are partly united at the base. The shape and color of the upper (open) petals is an opaque light green 2.5 GY (7/8) while the underside of them is 2.5 GY (8/6). The petals and sepals are acute elliptic in shape at tip and fused at the base, and range from 0.263 to 0.276 inches long, with the observed one being 0.272 inches. Width varies from 0.125 inches to 0.132 inches thereof. Both petals and sepals have a smooth texture on both the upper and lower surfaces. Pedicels range in length from 0.10 to 0.12 inches with observed one being 0.10 inches. The diameter ranges from 0.04 to 0.043 inches with the observed unit being 0.041 inches and color is 2.5 GY (7/8).

*Flower functionality*.—This tree exhibits a Type B flowering habit wherein the flower first opens in the female stage (i.e., functionally female) during the afternoon. The same flower then opens the next morning in the male stage wherein the three stamens covering the ovary, dehisce (release pollen). All 50 observed flowers viewed on two successive days, operated in like manner. As to the pistil, there is but one central pistil, which may vary in length from 0.15 inches to about 0.197 inches. The length of the ovary is within the range of 0.0666 inches to 1.085 inches and has a diameter of from 0.052 inches to 0.093 inches. The color of each is olive green on the order of 5Y (8/6). There are 9 stamens and 3 staminoids, with the outer stamen ranging from 0.132 inches to 1.019 inches lengthwise, and 0.197 inches to 0.026 inches in width. While the observed stamen was 0.194 inches long by 0.026 inches wide of green color 2.5GY (7/8). The anther of each stamen and some staminoids exhibited a brownish color of 5R (4/4).

*Peduncle*.—Peduncles are found to vary in length from 2.8 inches to 4.4 inches, with the observed unit being 3.6 inches. Peduncle diameter is within the range of 0.233 inches to 0.415 inches, and the observed unit was 0.401 inches. The insertion at the base of the fruit is a bit wider than the balance of the peduncle. The observed peduncle has a diameter of 0.415 inches and is 0.526 inches long. The 'Buck 3' fruit peduncle is inserted asymmetrically into the fruit and is mostly conical in shape. In contrast, the peduncle of the fruit from the parent tree 'Choquette' is centrally inserted into the fruit.

Figure 2:
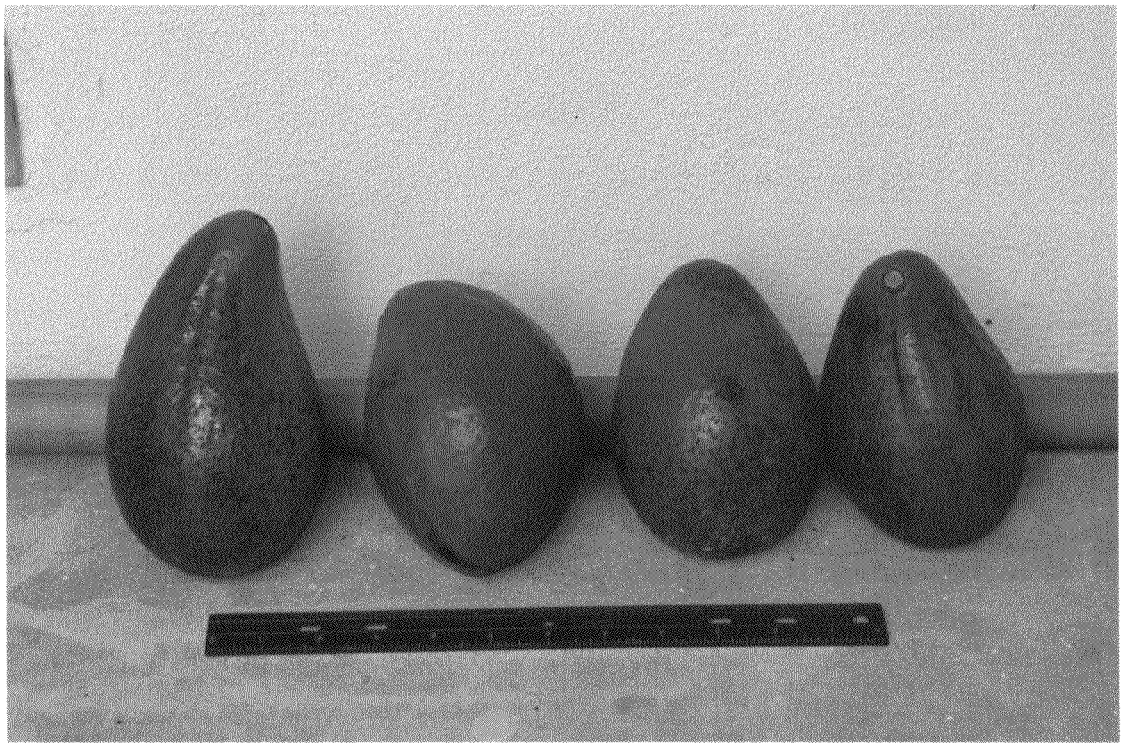
FIG. 2 is a color photograph showing the diversity of shapes of the avocado tree of this patent application.
Figure 3:
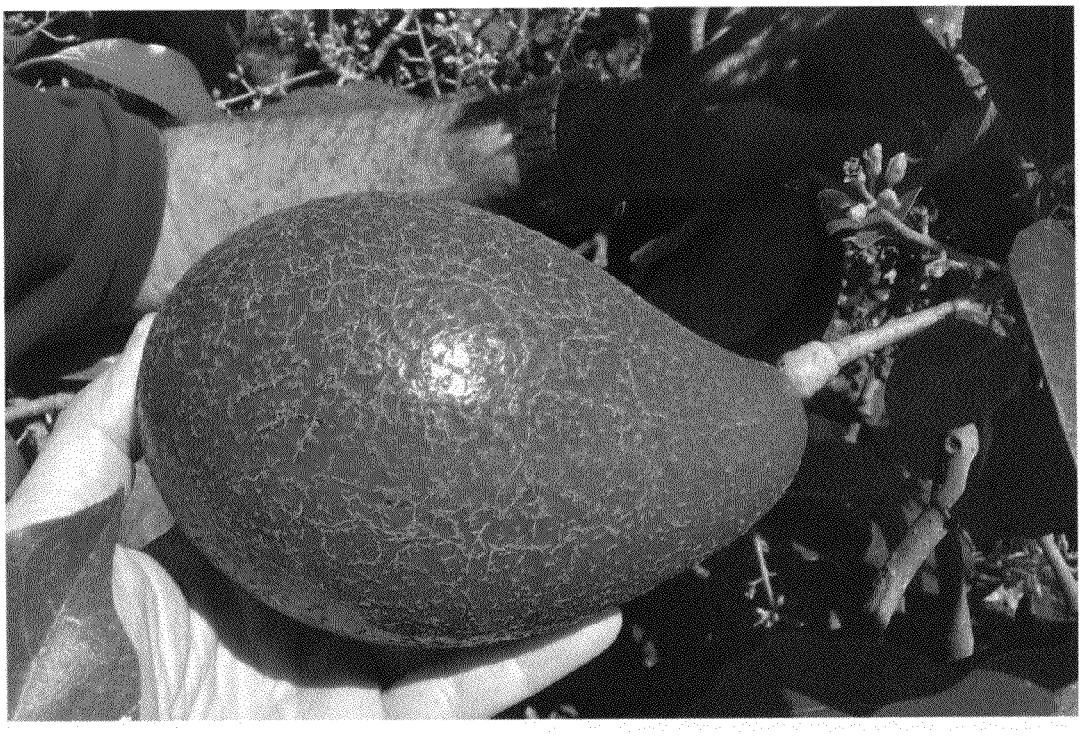
FIG. 3 is a color photograph of the skin of the fruit showing the large lenticels found on the skin as the fruit ripens.

*Fruit*.—Shape: obovate, with a small flattened area toward the apex on one side. See FIG. 2. fruit. As fruit ripen the lenticels become more pronounced (brown color) and peel color darkens. That is from a grayish brown to brown, 2.5Y (7/2 to 6/4). Fruit quality is excellent with a buttery, smooth flesh and with an excellent nutty flavor. As to size, whole fruit were found to vary from 9.3 ounces, to 23.63 ounces. The average unit weighed 18.6 ounces. The fruit from the parent 'Choquette' tree is elliptically shaped with a flattened area obliquely toward the apex, and is harvested firm late September to mid-January. 'Choquette' fruit are very large (18-40 oz.). In comparison, the 'Buck 3' fruit is obovate shaped with a small flattened area toward the apex on one side and weighs from 9.3 to 23.6 oz. per fruit.

Figure 4:
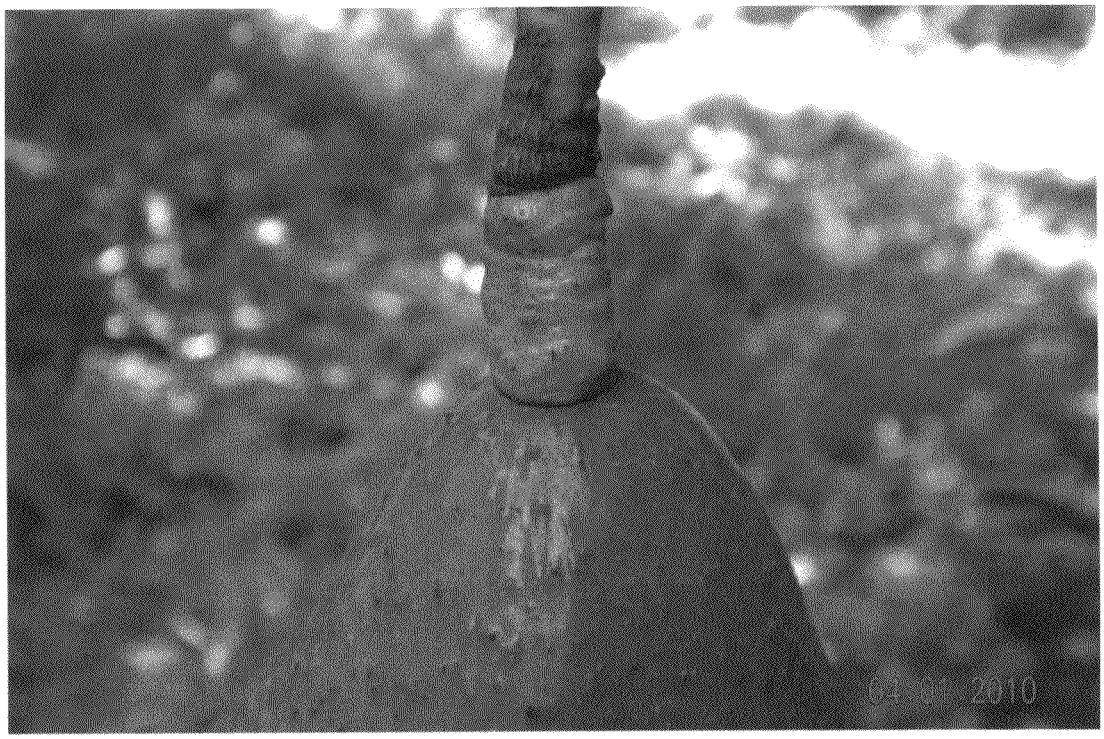
FIG. 4 is a closeup color photograph showing the pedicel size, shape and insertion.

Stem insertion and shape: The pedicel is inserted asymmetrically and is mostly conical, with some being cylindrical. See FIG. 4. Flower pedicels are 2.0 to 2.8 mm long and 0.1 to 0.2 mm in diameter; color, olive green (CCCC99) (Coutsoukis, 2004).

Size: Medium to medium large, average fruit weight is 526.7 g (18.6 oz) with a range of about 262 to 668 g (9.3 to 23.6 oz). The fruit size and shape are similar to those of 'Nesbitt', which ranges in size from 398 to 625 g (14 to 22 oz) and 81 to 95 mm (3 3/16 to 3 12/16 inches) in diameter.

Fruit shape and weight: The fruit of the 'Buck 3' is shaped differently from he fruit of both the 'Wheeling' and the 'Alfa' varieties of avocados. Whereas 'Wheeling' is spheroid shaped, and the 'Alfa' is narrowly obovate, the 'Buck 3' is obovate shaped with a small flattened area toward the apex on one side of the fruit piece. The 'Wheeling' fruit weighs from about 12 to 16 oz, and the 'Alfa' fruit weighs 15-20 oz. Whereas, the 'Buck 3' has an average weight of 18.6 oz with a broad range of weight of from 9.3 oz to 23.6 ounces.

TABLE 1

WEIGHT AND SIZING TABLE

| | Metric units | English units | |
|---|---|---|---|
| Parameter | Average /Range | Average | Range |
| Whole fruit | 526.7 g/262.1-668.1 g | 18.6 oz | 9.3-23.6 oz |
| Pulp | 247.0 g/189.1-503.1 g | 8.7 oz | 6.7 - 17.8 oz |
| Seed | 73.6 g /44.8-123.1 g | 2.6 oz | 1.6 -4.3 oz |
| Peel | 50.4 g/29.3-60.9 g | 1.8 oz | 1.0 - 2.2 oz |
| Fruit diameter | 9.1 cm /8.2-9.9 cm | 3 9/16 inch | 3 3/16-3 14/16 inch |
| Peel thickness | 1.7 mm | 1.3-3.0 mm | 0.8/16-2/16 inch |

Peel: Average peel weight is 50.4 g (1.8 oz). Average peel thickness is 1.7 mm (1/16 inch). Peel is stock green to forest green (green to dark green) (Hall Color Charts, 2004) or 336600 to 003300 (Coutsoukis, 2004); slightly rough but smooth on the flattened area located toward the base (stylar end) of the fruit. A longitudinal lettuce colored (Hall Color Charts, 2004) 66CC00 to 66CC33 (Coutsoukis, 2004) streak may be present on most fruit. The fruit peel of 'Buck 3' is slightly leathery and rough with longitudinal ridges as compared to the leathery and nearly smooth peel with undulations as found in the 'Choquette' and also as compared to the thick and hard shell like rough peel of the 'Alfa' variety and further compared to the hard shelled but smooth peel of the 'Wheeling' avocado.

Pulp: Averages about 46.9%. Ration of pulp weight to seed weight is 3.4. Pulp weight average is 247 g (8.7 oz). Thickness generally medium, however in some fruit a little less than medium and ranges from 2.86 to 3.7 cm (1 2/16-1 7/16 inch).

Figure 5A:
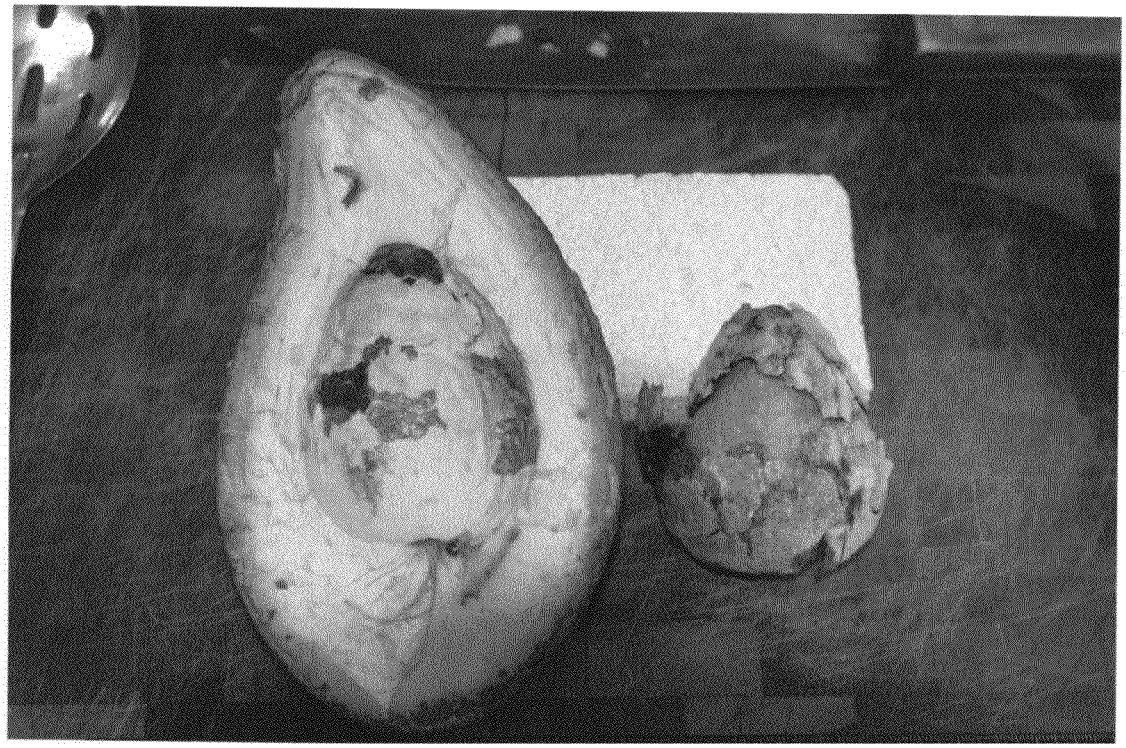
FIG. 5A and FIG. 5B are color photographs of the two fruits from the same tree, showing the color of the flesh and two different shape seeds.
Figure 5B:
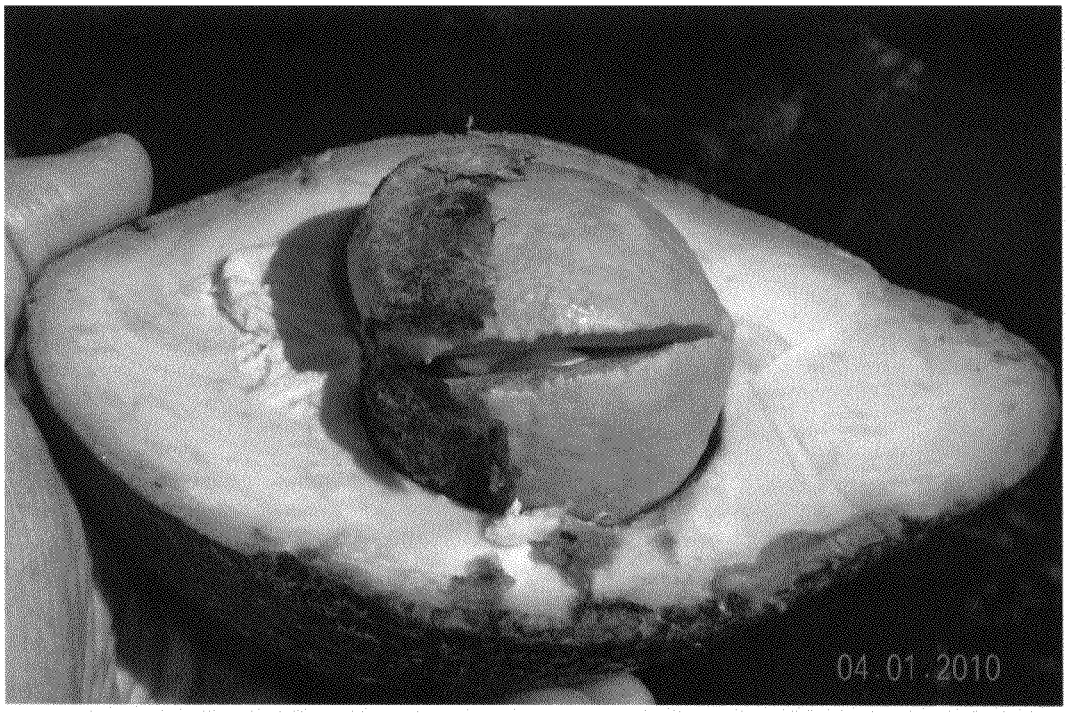

*Color*.—Dark green thin ring about 6 mm (¼ inch) adjacent to the peel — Granny Smith Apple Green, Sheen Green or Forest Green (Crayola, 2004) — and pulp color near seed is deep yellow. See FIG. 5.

*Consistency*.—Smooth and buttery without fibers.

Seed: Medium size, rounded to pear shaped (range 44.9-123.1 g; average 2.6 oz) The seed is medium size (average, 73.6 g; range 44.9-123.1 g; average, 2.6 oz; range 1.6-4.3 oz) and 5.6 cm by 6.4 cm (2 3/16×2 8/16inch). The seed is tight (not loose) in the cavity and average seed weight is 14% of total fruit weight. Seed coat color is brown per FIG. 5 — that is, brown to Sienna brown (Crayola , 2004) — and does not adhere to pulp early in the season but may adhere later in the season.

Harvest and production: Mature fruit may be harvested from late March to mid-May. On average the time from harvest to ripening (softening) at room temperature (~24degrees C.; 75 degrees F.) took 8.5 days with a range of 5 to 14 days. The "Buck 3" avocado tree bears every year but one year has a very heavy crop and the other a lighter crop, the lighter one being about 37.4 kg (82.5 lbs; 1.5 bushels). 'Buck 3' fruit matures from mid-March through mid-May. In contrast, 'Choquette' fruit matures from late September t mid-January, while 'Wheeling' matures from February to early March, and the 'Alfa' variety matures during the month of March. Thus the 'Buck 3' avocado is noteworthy because it matures much later than 'Choquette' later than 'Wheeling', and later than 'Alfa'. 'Buck3' is believed to be the latest maturing avocado found in Florida. In addition, during the flowering period in February through early May, 'Buck 3' trees also possess mature fruit and new vegetative flush, but the parent tree 'Choquette' tree does not.

Because of the outstanding and unique horticultural characters, especially its very late harvest season, this cultivar can be planted to extend Florida's avocado season. Although this new variety of avocado possesses the above described characteristics, it is to be understood that variations and fluctuations may occur in the magnitude and characteristics thereof due to changes ingrowing and climate conditions, irrigation and fertilization , pruning and pest control.

What is claimed is:

1. A new and distinct variety of avocado tree substantially as illustrated and described which is characterized by its late harvest season, variation in stone shape, and fine eating quality with non-fibrous flesh.

* * * * *